United States Patent
Ferrant et al.

(10) Patent No.: US 6,597,762 B1
(45) Date of Patent: Jul. 22, 2003

(54) METHOD AND APPARATUS OF LESION DETECTION AND VALIDATION BASED ON MULTIPLE REVIEWS OF A CT IMAGE

(75) Inventors: Matthieu D. Ferrant, Saint Remy les Chevreuse (FR); Mirelle Audet, Milon la Chapelle (FR); Saad A. Sirohey, Pewaukee, WI (US); Kelly L. Karau, New Berlin, WI (US); Beth A. Heckel, Sturtevant, WI (US); Cheryl R. Jones, Hubertus, WI (US); Ricardo S. Avila, Clifton Park, NY (US)

(73) Assignee: GE Medical Systems Global Technology Co., LLC, Waukesha, WI (US)

( * ) Notice: Subject to any disclaimer, the term of this patent is extended or adjusted under 35 U.S.C. 154(b) by 0 days.

(21) Appl. No.: 10/065,900

(22) Filed: Nov. 27, 2002

(51) Int. Cl.⁷ .............................. A61B 6/03; G01N 6/03; G01N 23/083
(52) U.S. Cl. .............................. 378/62; 378/8; 378/901
(58) Field of Search .............................. 378/8, 37, 62, 378/901

(56) References Cited

U.S. PATENT DOCUMENTS 5,255,187 A   10/1993  Sorensen
5,823,993 A * 10/1998  Lemelson .................... 604/503
5,917,929 A    6/1999  Marshall et al.
6,266,435 B1   7/2001  Wang
6,434,262 B2   8/2002  Wang

* cited by examiner

Primary Examiner—David V. Bruce
(74) Attorney, Agent, or Firm—Ziolkowski Patent Solutions Group, LLC; Michael A. Della Penna; Carl B. Horton

(57) ABSTRACT

An object detection apparatus includes a data acquisition system configured to acquire diagnostic data of the subject, an image reconstructor configured to reconstruct at least one image of the subject from the diagnostic data, and a data retrieval device configured to retrieve a first set of bookmarks identifying a first set of objects of interest in the at least one image. The object detection apparatus further includes a computer programmed to display the at least one image on a console and detect input from the user corresponding to a second set of bookmarks identifying a second set of objects of interest in the image. The computer is further programmed to selectively allow the user to incorporate each bookmark of the first set of bookmarks into the second set of bookmarks.

26 Claims, 3 Drawing Sheets

METHOD AND APPARATUS OF LESION DETECTION AND VALIDATION BASED ON MULTIPLE REVIEWS OF A CT IMAGE

BACKGROUND OF INVENTION

The present invention relates generally to CT imaging and, more particularly, to a method and apparatus of detecting and validating lesions in a CT image.

CT imaging is commonly used to provide diagnostic images of a medical patient for subsequent review by a radiologist or other health care provider to identify potentially cancerous lesions in the patient. An anatomical region susceptible to cancerous lesions is the lung anatomy and therefore a number of applications have been developed for automatically segmenting and sizing lung lesions that have been identified by a radiologist. Once such application is the CT Advanced Lung Analysis developed by the General Electric Company. Notwithstanding the advances achieved by the CT Advanced Lung Analysis tool, radiology productivity and accuracy may be comprised as the imaging data per anatomical volume increases. That is, advances in CT imaging technology are allowing for thinner image slices and, therefore, more image data per anatomical volume. With the increase of data to be reviewed by the radiologist, assuming a fixed amount of time, the accuracy of the radiologist may also become compromised. Therefore, there is an increasing need for secondary reading reconciliation tools such as computer aided detection schemes as high throughput, large quantity screening data becomes available.

Known detection tools such as the Advanced Lung Analysis provide tremendous capability for radiologist to identify lesions with bookmarks and two-and three-dimensional views. These tools also allow the radiologist to navigate through these bookmarks within a volumetric exam. As such, the radiologist can more effectively and efficiently identify lesions through the display of different view orientations (such as axial, coronal, sagital, or oblique 2D views) and types (maximum intensity projection, volume rendering, and the like) in given layout pre-sets.

Because of the importance of early detection of cancerous lesions, a number of protocols require a secondary review of each diagnostic image generated of the subject. The primary radiologist must then consider the results of the secondary review when making a final determination of lesion presence. However, this secondary review process requires additional review time by the primary radiologist to render a diagnosis; a problem exacerbated as image volume increases.

With the emergence of computer aided detection tools, there increasingly is a need for a graphical user interface (GUI) and a particular layout to visualize secondary reading results of an image to allow a radiologist to compare his or her reading with the reading of a secondary reviewer. Such a tool would provide a logical work flow for the review of CT images and therefore enable a radiologist to efficiently and effectively identify lesions in a CT image.

BRIEF DESCRIPTION OF INVENTION

The present invention is directed to a method and apparatus of detecting and confirming lesions in a CT image overcoming the aforementioned drawbacks. The present invention provides a GUI that allows a radiologist or other medical provider to provide an initial reading of a CT image and thereby indicate those objects of interest that may be lesions. The GUI further allows the radiologist to view those lesions or corresponding bookmarks relative to lesions or objects of interest identified by a secondary user. The secondary review may be completed using a computer aided detection process or the results of a manual review by a separate radiologist. As such, the present invention allows the radiologist to selectively accept or reject those objects of interest identified in the secondary review of the CT image into the primary review of the CT image to generate a final set of bookmarks corresponding to those objects in the CT image that may be considered lesions or other anomalies of concern.

Therefore, in accordance with one aspect of the present invention, an object detection apparatus includes a data acquisition system (DAS) configured to acquire diagnostic data of the subject, an image reconstructor configured to reconstruct at least one image of the subject from the diagnostic data, and a data retrieval device configured to retrieve a first set of bookmarks identifying a first set of objects of interest in the at least one image. The object detection apparatus further includes a computer programmed to display the at least one image on a console and detect input from the user corresponding to a second set of bookmarks identifying a second set of objects of interest in the image. The computer is further programmed to selectively incorporate each bookmark of the first set of bookmarks into the second set of bookmarks.

In accordance with another aspect of the present invention, a computer readable storage medium is provided and has thereon a computer program for determining similarities and differences between separate examinations of a diagnostic image. The computer program includes a set of instructions that when executed by a computer causes the computer to access imaging data from a DAS and display an image of a subject from the imaging data for examination. The computer is further caused to bookmark a primary set of objects of interest based on a set of inputs from a user. The set of instructions further causes the computer to access from memory a secondary set of objects of interest from a separate examination of the image and prompt the user to select each of the secondary set of objects. The computer is also caused to generate a final set of objects of interest from the primary set of objects of interest and the accepted objects of interest from the secondary set of objects of interest.

According to another aspect of the present invention, a method of determining lesion presence in an image of a subject includes the steps of reviewing a diagnostic image of a subject and identifying a first set of lesions in the diagnostic image. The method further includes the steps of bookmarking the first set of lesions and retrieving bookmarks corresponding to a second set of lesions identified in a separate review of the diagnostic image. The method also includes the steps of navigating through the bookmarks for the second set of lesions and selectively incorporating bookmarks from the second set of lesions with bookmarks from the first set of lesions. A final set of bookmarks corresponding to a final set of lesions believed to be present in the diagnostic image is then generated.

In accordance with yet a further aspect of the present invention, a lesion detection tool comprises means for assigning bookmarks to a first set of lesions in a diagnostic image. The lesion detection tool further includes means for retrieving bookmarks for a second set of lesions identified in a separate review of the diagnostic image as well as means for selectively incorporating bookmarks from the second set of lesions into the bookmarks for the first set of lesions.

Various other features, objects and advantages of the present invention will be made apparent from the following detailed description and the drawings.

BRIEF DESCRIPTION OF DRAWINGS

The drawings illustrate one preferred embodiment presently contemplated for carrying out the invention.

In the drawings.

DETAILED DESCRIPTION

The present invention will be described with respect to detection and validation of lesions in the lung anatomy of a medical patient using a CT imaging system. However, the present invention is equivalently applicable for the detection and confirmation of lesions or other objects of interest in other anatomies of a medical patient or other subject. Additionally, the present invention may be implemented with other imaging systems such as x-ray systems and other diagnostic imaging systems. Further, the present invention may also be equivalently implemented in a non-medical environment such as airport baggage inspection systems and postal inspection systems for the detection and validation of objects of interest.

Figure 1:
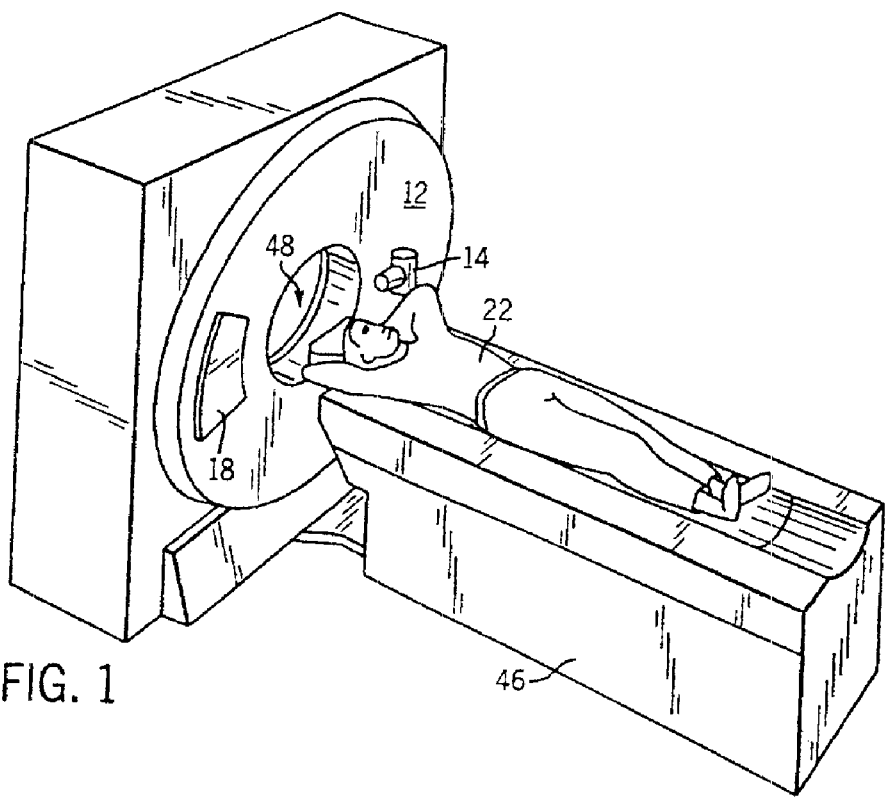
FIG. 1 is a perspective view of a CT imaging system.
Figure 2:
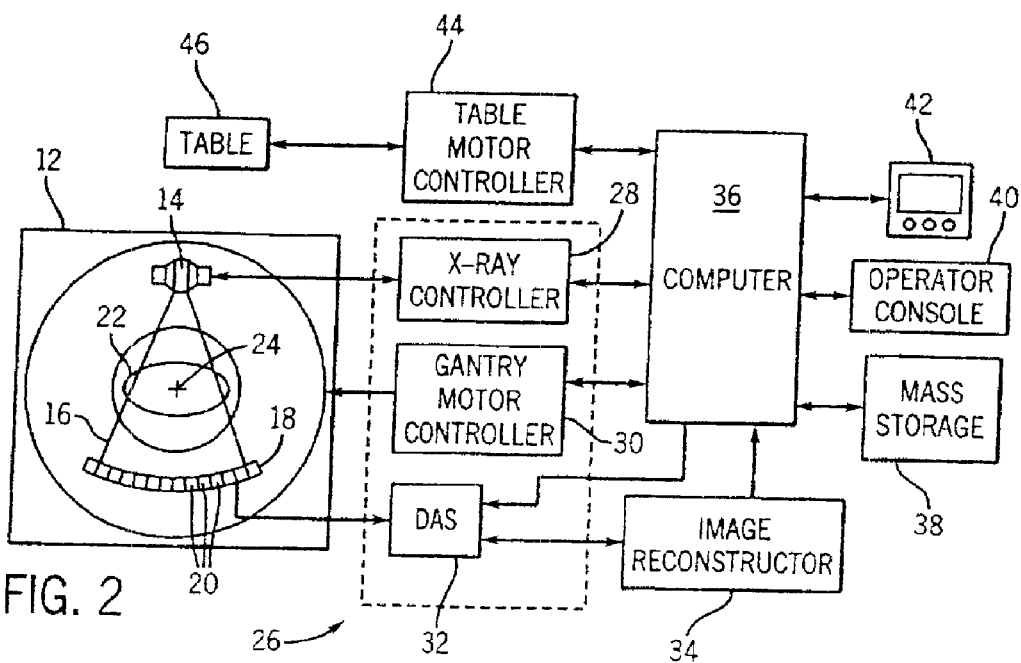
FIG. 2 is a schematic representation of the CT system shown in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of the gantry 12. Detector array 18 is formed by a plurality of detectors 20 which together sense the projected x-rays that pass through a medical patient 22. Each detector 20 produces an electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

Figure 3:
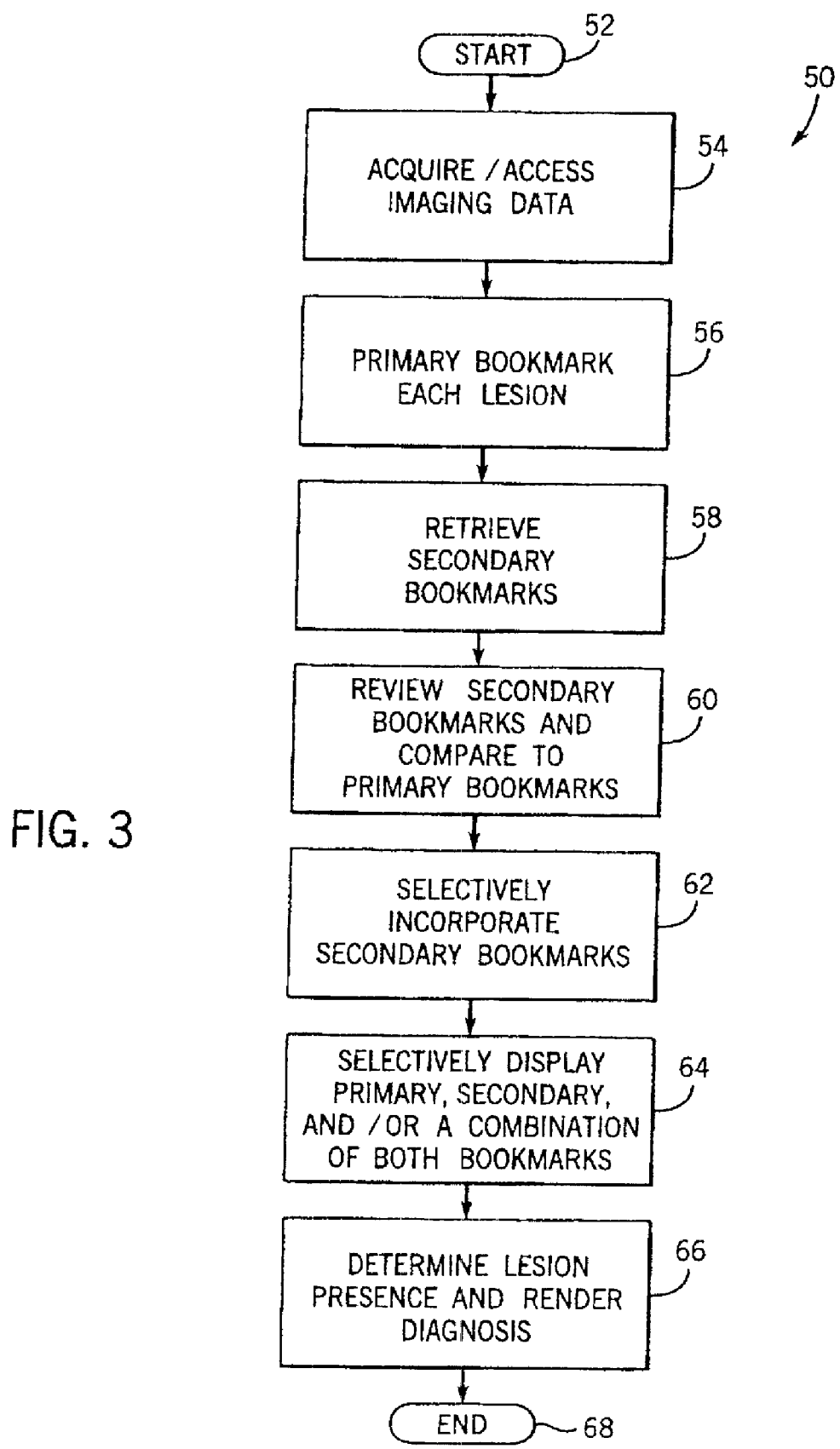
FIG. 3 is a flow chart setting forth the steps of a lesion detection and confirmation process in accordance with the present invention.

Referring now to FIG. 3, the steps of a process SO for identifying and confirming lesions in a CT image are provided. The process 50 will be described with respect to a method of detection and confirmation, however, the steps of the method may be equivalently implemented as acts achieved by a computer based on a set of instructions of a computer program. Process 50 begins at 52 with the acquisition and/or accessing of imaging data 54. The imaging data may be acquired from a CT system or other imaging system or accessed from memory of the imaging system or other storage medium. That is, imaging data or images from a previous imaging session may be stored in an archival facility and accessed from that facility for use by the present invention. Once the imaging data is accessed 54, an image is displayed on a GUI (FIG. 4) for subsequent evaluation by a radiologist or other user. The radiologist may visualize the image or series of images in a single magnified view or in a number of normally sized views showing data along different orientations such as oblique, axial, coronal, and sagital. Additionally, it is contemplated for the user to interactively increase the slice thickness of the displayed image to show larger portions of any vessels of the lung anatomy and highlight objects of interest or nodules and isolated spheres or profusions along vessels or the pleura.

Following the display of the image or series of images, the radiologist may then place bookmarks 56 on any of the views. That is, the user may navigate through each of the images at the various views to locate particular objects of interest and bookmark 56 those objects of interest as possible lesions or other nodal anomalies. Additionally, with the placement of each bookmark or highlighting of each object of interest, a bookmark list is generated identifying the location and number of the identified object. As will be described with respect to FIG. 4, the user may then navigate the bookmark list to quickly view those objects of interest that have previously been identified.

Still referring to FIG. 3, once the radiologist completes the primary review of the images 56, the radiologist can then retrieve results of a secondary review of the same imaging data at 58. The secondary review or reading of the imaging data may either be performed by another radiologist or by a computer aided detection system designed to identify bookmark lesions in an image. During the secondary review of the imaging data, the secondary reviewer also bookmarks objects of interest during the review process. Those bookmarks are stored and associated with the secondary review so that a primary radiologist can then access those bookmarks to compare results of a primary review 60.

To improve the efficiency of the lesion detection process, duplicate bookmarks are automatically identified and reconciled. Each set of bookmarks is scanned relative to one another to determine if the primary radiologist and the secondary reviewer have identified common lesions. If so, the secondary bookmark corresponding to the commonly identified lesion is preferably not displayed on the GUI. It is contemplated, however, that the duplicate bookmarks could be color-coded or commonly shaped to provide feedback to the primary radiologist that the computer aided detection system or the secondary reviewer identified similar lesion areas to those identified by the primary radiologist in the primary review of the image. The automatic identification of the duplicate bookmarks is not a trivial process because each reviewer could identify the same lesion but place the bookmark on a different portion of that lesion during the review process. Therefore, the process includes the verification that the duplicate bookmarks do, in fact, correspond to a common lesion rather than separate lesions.

Automated duplication finding allows the user to not only check those lesions missed in the primary review but also those that the secondary reader found. For bookmarks that are close to each other, a first pass to re-estimate the center of the nodule is made followed by a check to determine if the found centers are the same for both bookmarks, which would indicate both bookmarks point to the same nodule. This automatic center determination is based on a first bounding box size estimation, which is done by computing cumulated histograms along each direction from the bookmark's center. The box size is determined so that the cumulated histogram along each direction includes a significant portion of foreground and background (tissue and parenchyma). Next, a distance transform is computed from a binarized shape (discriminating between background parenchyma and the foreground soft tissue, vessel, nodule) within the computed bounding box, and the best center maximizing the distance to the edges is found inside the nodule. The procedure is executed for both bookmark locations, and if the found center is identical, the bookmark locations match thereby indicating a duplicate.

When the secondary set of bookmarks is imported into the GUI, each of the secondary bookmarks may be assigned a common color or shape so that the radiologist or primary reviewer can delineate between those bookmarks that were identified by the secondary review and those bookmarks corresponding to the primary review. As such, the primary reviewer or primary radiologist then navigates using common GUI navigational tools through each of the secondary bookmarks. As the radiologist is reviewing the bookmarks or lesions compiled during the secondary review, the radiologist is prompted to either accept or decline incorporation of each secondary bookmark into the list of primary bookmarks at 62. Alternately, the radiologist may also dismiss each of the secondary bookmarks. The "dismissal" of a secondary bookmark does not delete the secondary bookmark as a declination would, but simply does not incorporate the secondary bookmark into the primary set of bookmarks. Simply, a "dismissal" allows the primary radiologist to review the bookmark again at a later time to make an incorporation decision.

As previously described, after importation of the secondary bookmarks onto the GUI, each of the secondary bookmarks is assigned a shape or color to differentiate between the primary or first set of bookmarks. However, as the radiologist or primary reviewer selectively incorporates or accepts each of the secondary bookmarks at 62, the selected or accepted secondary bookmark changes shape and/or color to correspond to the color and/or shape given to the primary set of bookmarks. As such, the process automatically provides feedback to the primary radiologist as to which bookmarks have been incorporated as well as those lesions that have been identified by the secondary reviewer but not incorporated.

Once the primary reviewer or radiologist has completed navigating through each of the secondary set of bookmarks, a final set of bookmarks is compiled. The final set of bookmarks which correspond to those objects of interest that the primary reviewer considers to be lesions or other anatomical anomalies of concern includes the first set of bookmarks or those bookmarks identified by the primary radiologist during the first review of the image as well as the bookmarks of the secondary review that were accepted by the primary reviewer during the review of the secondary review. While the default is to display the final set of bookmarks and corresponding lesions 64, the present invention contemplates a display of the primary, secondary, duplicate, or a combination thereof bookmarks. After the final set of bookmarks has been compiled, the radiologist or other medical professional can then make a diagnosis 66 as to the occurrence of lesions or other objects of concern in the image knowing that a second review of the image was completed and that the second review of the image was also reviewed in forming the diagnosis. The process is complete at step 68.

Figure 4:
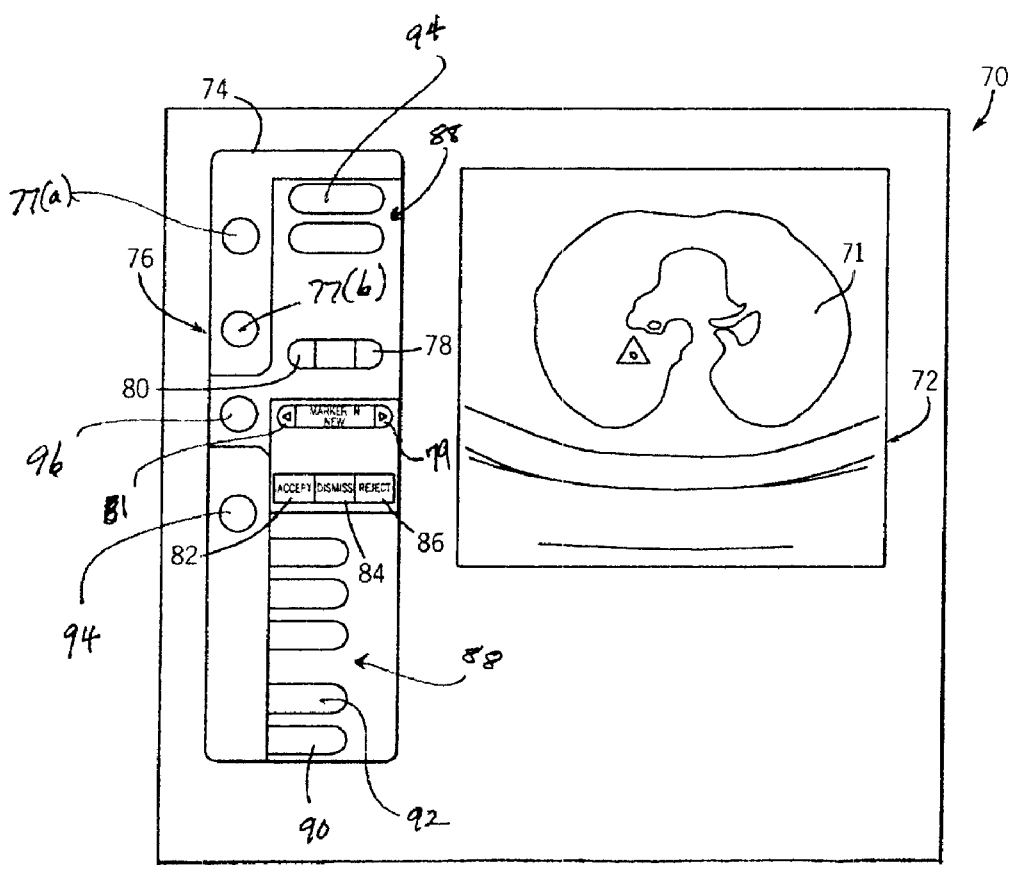
FIG. 4 is a representation of a GUI in accordance with the present invention.

Referring now to FIG. 4, a GUI 70 in accordance with the present invention is shown. GUI 70 provides a platform for the radiologist to not only identify or bookmark objects of interest in an image but to also review the bookmarks of the secondary review of the image. The GUI is constructed according to known techniques and includes a portion 72 for displaying the image(s) 71 that is the subject of the review. A navigational bar 74 is also provided on the GUI 70 and includes a series of buttons 76 that allow the primary reviewer to navigate through the various bookmarks identified during the primary review as well as the secondary review of the image. For example, selection of button 77(a) will display the primary bookmarks from the primary review whereas button 77(b) will display the secondary bookmarks from the secondary review. The navigational tool also includes a "Next" button 78 for displaying the next image as well as "Previous" button 80 for displaying the previous image. A Forward button 79 is provided to view the next bookmark and corresponding lesion. A "Reverse" button 81 allows the user to display the previous bookmark(s) and corresponding lesion(s). When each bookmark and corresponding object of interest is displayed, an "Accept" button 82, a "Dismiss" button 84, and a "Decline" button 86 are activated to allow the radiologist to selectively incorporate each of the secondary bookmarks into the list of primary bookmarks, as was described with respect to FIG. 3. The final set of bookmarks corresponds to a final list of the objects of interest that he: primary radiologist considers lesions or other anomalies of concern. Additional buttons 88 may include a text entry button 90 that when selected allows the primary radiologist to input notes or comments relating to a particular bookmark or corresponding object of interest. The additional buttons may also include a "Display Duplicate Bookmarks" button 92. A "Patient Identifier" button 94 allows the radiologist to review patient information when reviewing the bookmarks and corresponding objects of interest. A button 94 for saving changes to the bookmark list is also included on the GUI. As such, an "Open" button 96 for retrieving the results of previous review is also provided. The aforementioned buttons and layout illustrate one embodiment in which GUI 70 may be presented. Other buttons and other layouts are contemplated and within the scope of the invention.

While the present invention has been described with respect to the detection and validation of lesions in the lung anatomy of a medical patient, the present invention is equivalently applicable for the detection of other objects of interest in a medical patient or other subject. For example, the present invention could be used to identify and validate objects of interest or concern in a baggage handling system or postal inspection system for security purposes. The present invention could also be used as a training tool to train radiologists in lesion detection.

Therefore, in accordance with one embodiment of the present invention, an object detection apparatus includes a data acquisition system (DAS) configured to acquire diagnostic data of the subject, an image reconstructor configured to reconstruct at least one image of the subject from the diagnostic data, and a data retrieval device configured to retrieve a first set of bookmarks identifying a first set of objects of interest in the at least one image. The object detection apparatus further includes a computer programmed-to display the at least one image on a console and detect input from the user corresponding to a second set of bookmarks identifying a second set of objects of interest in the image. The computer is further programmed to selectively incorporate each bookmark of the first set of bookmarks into the second set of bookmarks.

In accordance with another embodiment of the present invention, a computer readable storage medium is provided and has thereon a computer program for determining similarities and differences between separate examinations of a diagnostic image. The computer program includes a set of instructions that when executed by a computer causes the computer to access imaging data from a DAS and display an image of a subject from the imaging data for examination. The computer is further caused to bookmark a primary set of objects of interest based on a set of inputs from a user. The set of instructions further causes the computer to access from memory a secondary set of objects of interest from a separate examination of the image and prompt the user to select each of the secondary set of objects. The computer is also caused to generate a final set of objects of interest from the primary set of objects of interest and the accepted objects of interest from the secondary set of objects of interest.

According to another embodiment of the present invention, a method of determining lesion presence in an image of a subject includes the steps of reviewing a diagnostic image of a subject and identifying a first set of lesions in the diagnostic image. The method further includes the steps of bookmarking the first set of lesions and retrieving bookmarks corresponding to a second set of lesions identified in a separate review of the diagnostic image. The method also includes the steps of navigating through the bookmarks for the second set of lesions and selectively incorporating bookmarks from the second set of lesions with bookmarks from the first set of lesions. A final set of bookmarks corresponding to a final set of lesions believed to be present in the diagnostic image is then generated.

In accordance with yet a further embodiment of the present invention, a lesion detection tool comprises means for assigning bookmarks to a first set of lesions in a diagnostic image. The lesion detection tool further includes means for retrieving bookmarks for a second set of lesions identified in a separate review of the diagnostic image as well as means for selectively incorporating bookmarks from the second set of lesions into the bookmarks for the first set of lesions.

The present invention has been described in terms of the preferred embodiment, and it is recognized that equivalents, alternatives, and modifications, aside from those expressly stated, are possible and within the scope of the appending claims.

What is claimed is:

1. An object detection apparatus comprising:
a DAS configured to acquire diagnostic data of a subject;
an image reconstructor configured to reconstruct at least one image of the subject from the diagnostic data;
a data retrieval device configured to retrieve a first set of bookmarks identifying a first set of objects of interest in an image; and
a computer programmed to:
display the image on a console;
detect inputs from a user corresponding to a second set of bookmarks identifying a second set of objects of interest in the image; and
selectively incorporate each bookmark of the first set into the second set of bookmarks.

2. The object detection apparatus of claim 1 wherein the computer is further programmed to prompt a user to one of accept and reject each of the first set of bookmarks.

3. The object detection apparatus of claim 2 wherein the computer is further programmed to compile a final set of bookmarks based on the second set of bookmarks and the accepted bookmarks of the first set of bookmarks.

4. The object detection apparatus of claim 3 wherein the final set of bookmarks correspond to anomalies in the image.

5. The object detection apparatus of claim 4 wherein the anomalies include lesions in an anatomical region of a medical patient.

6. The object detection apparatus of claim 5 wherein the anatomical region includes a lung region of the medical patient.

7. The object detection apparatus of claim 1 wherein the computer is further programmed to:
display the first set of bookmarks and the second set of bookmarks; and
color differentiate the first set of bookmarks from the second set of bookmarks.

8. The object detection apparatus of claim 1 wherein the computer is further programmed to display the first set of bookmarks and the second set of bookmarks and assign a unique shape to one of the sets to visually differentiate between the sets of bookmarks.

9. The object detection apparatus of claim 1 wherein the computer is further programmed to automatically determine duplicates between the first set of bookmarks and the second set of bookmarks.

10. The object detection apparatus of claim 1 incorporated into a radiation based imaging system.

11. The object detection apparatus of claim 9 wherein the radiation based imaging system includes a CT system.

12. A computer readable storage medium having a computer program for determining similarities and differences between separate examinations of a diagnostic image stored thereon and includes a set of instructions that when executed by a computer causes the computer to:
access imaging data from a DAS;
display an image of a subject from the imaging data for examination;
bookmark a primary set of objects of interest based on a set of inputs from a user;
access from memory bookmarks for a secondary set of objects of interest from a separate examination of the image;
prompt the user to selectively accept each of the secondary set of objects of interest; and
generate a final set of objects of interest from the primary set of objects of interest and the accepted objects of interest from the secondary set of objects of interest.

13. The computer readable storage medium of claim 12 wherein the secondary examination of the image includes a review of the image by a secondary radiologist.

14. The computer readable storage medium of claim 12 wherein the set of instructions further causes the computer to:
display a copy of the image to another user; and
bookmark the secondary set of objects of interest based on a set of inputs from the another user.

15. The computer readable storage medium of claim 12 wherein the set of instructions further causes the computer to display a GUI with the image in a portion of the GUI and a navigation tool in another portion, the navigation tool configured to enable the user to view each of the primary and the secondary sets of objects of interest.

16. The computer readable storage medium of claim 15 wherein the set of instructions further causes the computer to visually differentiate the primary set of objects of interest and the secondary set of objects of interest from one another by color.

17. The computer readable storage medium of claim 15 wherein the set of instructions further causes the computer to visually differentiate the primary set of objects of interest and the secondary set of objects of interest from one another by shape.

18. The computer readable storage medium of claim 12 wherein the set of instructions further causes the computer to display at least one of an oblique, an axial, a coronal, and a sagittal view of the subject.

19. A method of determining lesion presence in an image of a subject, the method comprising the steps of:

reviewing a diagnostic image of a subject;

identifying a first set of lesions in the diagnostic image;

bookmarking the first set of lesions;

retrieving bookmarks corresponding to a second set of lesions identified in a separate review of the diagnostic image;

navigating through the bookmarks for the second set of lesions;

selectively incorporating bookmarks from the second set of lesions with bookmarks from the first set of lesions; and generating a final set of bookmarks corresponding to a final set of lesions believed to be present in the diagnostic image.

20. The method of claim 19 further comprising the step of differentiating between the first set of bookmarks and the second set of bookmarks by color.

21. The method of claim 20 further comprising the step of changing the color of a bookmark from the second set to the color of the first set if a corresponding lesion is selected to be incorporated into the first set of bookmarks.

22. The method of claim 19 further comprising the step of differentiating between the first set of bookmarks and the second set of bookmarks by shape.

23. The method of claim 22 further comprising the step of changing the shape of a bookmark from the second set to the shape of the first set if a corresponding lesion is selected to be incorporated into the first set of bookmarks.

24. The method of claim 19 wherein the diagnostic image includes an image from a lung area of the subject.

25. The method of claim 19 wherein the bookmarks for the second set of lesions are automatically generated with a computer aided detection system.

26. A lesion detection tool comprising:

means for assigning bookmarks to a first set of lesions in a diagnostic image;

means for retrieving bookmarks for a second set of lesions identified in a separate review of the diagnostic image; and means for selectively incorporating bookmarks from the second set of lesions into the bookmarks for the first set of lesions.

* * * * *